US00PP10004P

United States Patent [19]

Meilland

[11] Patent Number: Plant 10,004

[45] Date of Patent: Aug. 19, 1997

[54] HYBRID TEA ROSE PLANT NAMED 'MEITEBROS'

[75] Inventor: Alain A. Meilland, Antobes, France

[73] Assignee: The Conard-Pyle Company, West Grove, Pa.

[21] Appl. No.: 706,495

[22] Filed: Sep. 4, 1996

[51] Int. Cl.[6] ..... A01H 5/00

[52] U.S. Cl. ..... Plt./18

[58] Field of Search ..... Plt./18, 19

[56] References Cited

U.S. PATENT DOCUMENTS

P.P. 5,130 11/1983 Weeks ..... Plt./18

P.P. 7,561 6/1991 Twomey ..... Plt./18

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which abundantly forms attractive fragrant blossoms that are Venetian Pink suffused with Neyron Rose in coloration. Such blossoms are long-lasting and exhibit a good petal-drop propensity. The plant exhibits medium green and glossy foliage, as well as good disease resistance. The new variety is particularly well suited for growing as attractive ornamentation in the landscape.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the cross of the 'Perfume Delight' variety (U.S. Plant Pat. No. 3,282) and the 'Prima Ballerina' variety (non-patented in the United States). The male parent (i.e., The pollen parent) was the 'Meizeli' variety (U.S. Plant Pat. No. 8,391). The parentage of the new variety can be summarized as follows:

('Perfume Delight'×'Prima Balleria')×'Meizeli'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive long-lasting fragrant blossoms that are Venetian Pink suffused with Neyron Rose in coloration,
(b) exhibits a bushy growth havit,
(c) forms attractive medium green and glossy foliage,
(d) exhibits good disease resistance, and
(d) is particularly well suited for growing as attractive ornamentation in the landscape.

The new variety well meets the needs of the horiticultural industry and is particularly well adapted for use as an attractive ornamental plant in an outdoors environment.

The new variety has been found to undergo asexual propagation in France by a number of routes, including budding, grafting, and cuttage. Asexual propagation by the above-mentioned techniques in France has shown that the characteristics of the new variety are stable and are stirctly transmissible by such asexual propagation from one generation to another.

The new variety has been named the 'Meitebros' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rose froebelii* understock and growing outdoors at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflet—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

Figures 2, 3, 4, 5, 6, 7, 8, 9, 10, 11, 12, 13, 15, 16:
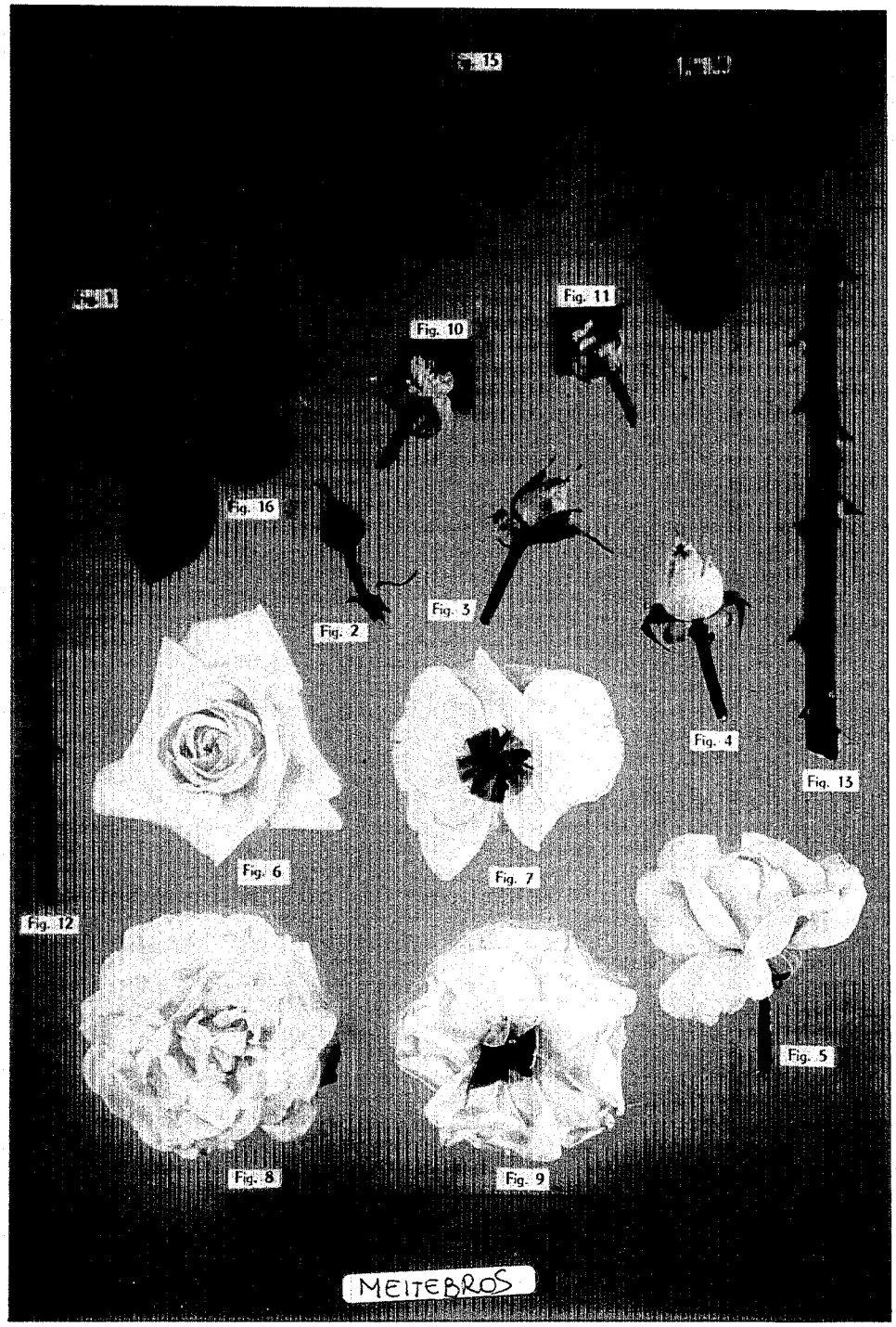

The chart used in the identification of the colors is that of The Royal Horticultural Society (R.H.S. Colour Chart). The description is based on the observation of three year-old plants during June while budded on *Rosa froebelii* understock and growing outdoors at Le Cannet des Maures, Var, France. The coloration in common terms precedes reference to the chart in some instances.

Class: Hybrid Tea.

Plant:

*Height.*—approximately 90 to 100 cm. on average at the end of the growing season.

*Habit.*—Bushy.

Branches:

*Color.*—Young stems: Yellow-Green Group 114A, and more or less maculated with reddish-brown coloration. Adult wood: Yellow-Green Group 146B.

*Thorns.*—Size: medium. Quantity: numerous. Color: pinkish on young stems and Havana brown on adult wood.

Leaves:

*Stipules.*—Adnate, pectinate, rather narrow and linear.

*Petioles.*—Upper surface: striped reddish on young foliage, and medium green on adult foliage with more or less glandular edges. Under surface: light green, and rarely bear small thorns.

*Leaflets.*—Number: 3, 5, and 7 (most often). Shape: oval. Serration: single and regular (as illustrated). Texture: consistent. General appearance: dense, medium green, and glossy. Color (young foliage): Upper surface: reddish brown. Under surface: reddish brown. Color (adult foliage): Upper surface: Green Group 137A. Under surface: Green Group 137C.

Inflorescence:

*Number of flowers.*—Usually one to three per stem.

*Peduncle.*—Light green more less stained with reddish coloration, and the length is approximately 5 cm. on average.

*Sepals.*—Upper surface: tomentose, and greenish in coloration. Under surface: medium green in coloration and with a few extensions.

*Buds.*—Shape: conical. Length: approximately 2.5 to 3 cm. on average. Size: medium. Color upon opening: Upper surface: near Shell Pink, Red Group 37C, and more or less suffused with greenish coloration. Under surface: near Shell Pink, Red Group 37C, and maculated with greenish coloration.

*Flower.*—Shape: cup-shaped. Diameter: approximately 8.5 to 9 cm. on average. Color (when opening begins): Upper surface: near Venetian Pink, Red Group 49C, and more or less suffused with Neyron Rose, Red Group 55C. Under surface: near Venetian Pink, Red Group 49C, and more or less suffused with Neyron Rose, Red Group 55C. Color (when blooming): Upper surface: near Venetian Pink, Red Group 49C, and more or less suffused with Neyron Rose, Red Group 55C. Under surface: near Venetian Pink, Red Group 49C, and more or less suffused with Neyron Rose, Red Group 55C. Color (at end of opening): Upper surface: near Ventetian Pink, Red Group 49C, and more or less suffused with Neyron Rose, Red Group 55C. Under surface: near Venetian Pink, Red Group 49C, and more or less suffused with Neyron Rose, Red Group 55C. Fragrance: strong. Lasting quality: very long on the plant. Petal number: approximately 40 to 45 on average. Petal shape: the base is oval and the tip is cordiform. Petal drop: very good with the petals commonly detaching cleanly. Stamen number: approximately 85 on average. Anthers: ochre in coloration. Filaments: bright yellow in coloration. Pistils: approximately 125 on average. Stigmas: Yellowish in coloration. Styles: yellowish in coloration. Receptacle: light green, smooth, and in longitudinal section in the shape of a wide pitcher.

Development:

*Vegetation.*—Very vigorous.

*Blooming.*—Very abundant and substantially continuous.

*Resistance to diseases.*—Very good particularly with respect to Marssonina and black spot.

*Resistance to frost.*—Good.

*Fructification.*—Good.

I claim:

1. A new and distinct variety of Hybrid Tea rose plant characterized by the following combination of characteristics:

(a) forms in abundance attractive long-lasting fragrant blossoms that are Venetian Pink suffused with Neyron Rose in coloration,
(b) exhibits a bushy growth habit,
(c) forms attractive medium green and glossy foliage,
(d) exhibits good disease resistance, and
(e) is particularly well suited for growing as attractive in the ornamentation in the landscape;

substantially as herein shown and described.

* * * * *

MEITEBROS